United States Patent
Vicari et al.

(10) Patent No.: US 9,145,297 B2
(45) Date of Patent: Sep. 29, 2015

(54) METHOD FOR PRODUCING ACETYLENE AND SYNTHESIS GAS

(71) Applicant: BASF SE, Ludwigshafen (DE)

(72) Inventors: Maximilian Vicari, Limburgerhof (DE); Christian Weichert, Bad Duerkheim (DE); Dirk Grossschmidt, Mannheim (DE); Michael Russ, Roemerberg (DE); Mirko Haider, Maxdorf (DE); Horst Neuhauser, Dudenhofen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/422,978

(22) PCT Filed: Sep. 2, 2013

(86) PCT No.: PCT/EP2013/068102
§ 371 (c)(1),
(2) Date: Feb. 20, 2015

(87) PCT Pub. No.: WO2014/037311
PCT Pub. Date: Mar. 13, 2014

(65) Prior Publication Data
US 2015/0217999 A1    Aug. 6, 2015

(30) Foreign Application Priority Data
Sep. 5, 2012 (EP) .................... 12183175

(51) Int. Cl.
*C01B 3/38* (2006.01)
*C01B 3/36* (2006.01)

(52) U.S. Cl.
CPC ......... *C01B 3/363* (2013.01); *C01B 2203/0255* (2013.01); *C01B 2203/0805* (2013.01); *C01B 2203/0877* (2013.01); *C01B 2203/0883* (2013.01); *C01B 2203/1235* (2013.01)

(58) Field of Classification Search
CPC .............................................. C01B 2203/0244
See application file for complete search history.

(56) References Cited

U.S. PATENT DOCUMENTS

| 3,242,225 A | 3/1966 | Danz et al. |
| 5,789,644 A | 8/1998 | Paessler et al. |
| 5,824,834 A | 10/1998 | Bachtler et al. |

FOREIGN PATENT DOCUMENTS

| DE | 14 18 664 | 11/1968 |
| DE | 44 22 815 | 1/1996 |

OTHER PUBLICATIONS

International Search Report issued Nov. 5, 2013, in PCT/EP13/068102 filed Sep. 2, 2013.

(Continued)

*Primary Examiner* — Melvin C Mayes
*Assistant Examiner* — Kenneth Vaden
(74) *Attorney, Agent, or Firm* — Oblon, McClelland, Maier & Neustadt, L.L.P.

(57) ABSTRACT

The invention proposes a method for producing acetylene and synthesis gas by partial oxidation of hydrocarbons with oxygen, wherein a first feedstock (1), containing one or more hydrocarbons, and a second feedstock (2), containing oxygen, —are preheated separately from one another, —are fed via a burner block (B) to a combustion chamber (F), in which the partial oxidation of the hydrocarbons takes place, —obtaining a cracked gas, which is quenched by injecting a quench oil downstream of the furnace body at 200° C. to 250° C., wherein —a flow of product gas Ig is obtained, which —is cooled in a burner column (BK) with further quench oil, obtaining —a flow of product gas IIg cooled to 60° C. to 90° C., which —is guided into a final cooler (SK), in which a flow of product gas IIIg, cooled to 20° C. to 50° C., is obtained by direct thermal exchange with water, as well as a flow of process water I liq —which is characterized in that the flow of process water I liq is subjected to purification by partial evaporation in a single-stage expansion chamber, wherein the flow of process water I liq is vaporized to a proportion of 0.01 percent by weight to 10 percent by weight, relative to the total weight of same, obtaining a purified flow of process water II liq which is removed in the waste water.

9 Claims, 1 Drawing Sheet

(56) References Cited

OTHER PUBLICATIONS

Friz, H., "Neuere Entwicklungen der Acetylen-Herstellung bei de BASF", Chemie Ingenieur Technik, vol. 40, No. 20, pp. 999-1004, XP055085331, Oct. 25, 1968.

"Ullmann's Encyclopedia of Industrial Chemistry", Fifth, Completely Revised Edition, Abrasives to Aluminum Oxide, vol. A 1, No. 20, pp. 97-145, Dec. 7, 1984.

"Ullmann's Encyclopedia of Industrial Chemistry", Wiley-VCH Verlag, 2008, Acetylenes, pp. 13-15.

Written Opinion issued Nov. 5, 2013 in PCT/EP2013/068102 filed Sep. 2, 2013 (English translation only).

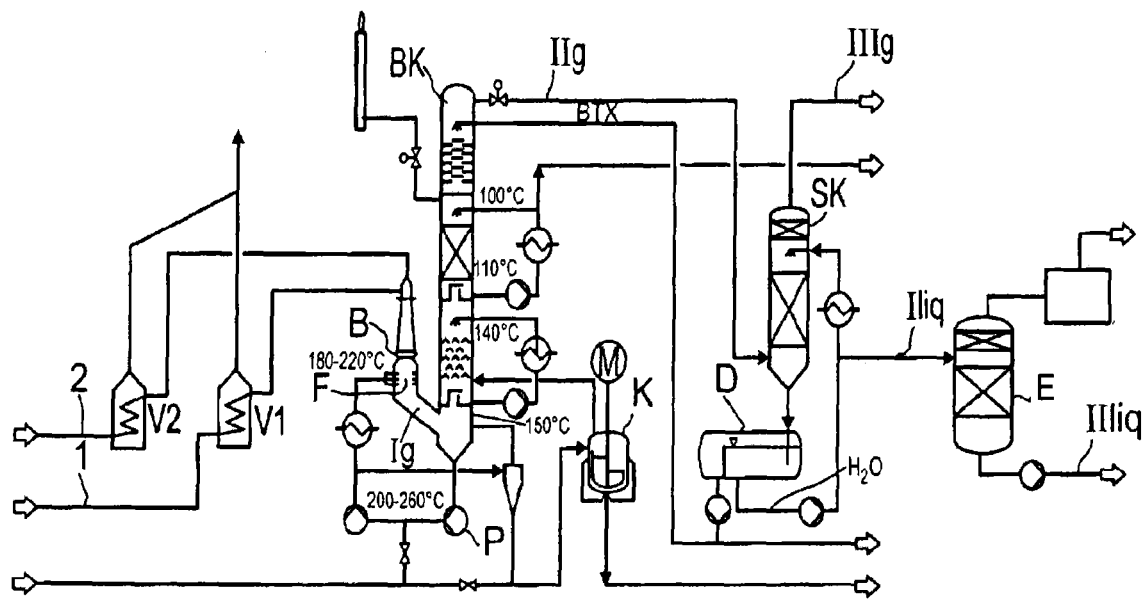

METHOD FOR PRODUCING ACETYLENE AND SYNTHESIS GAS

The present invention relates to a process for preparing acetylene and synthesis gas by partial oxidation of hydrocarbons with oxygen.

The above partial oxidation is a high-temperature reaction which is typically conducted in a reactor system comprising a mixing unit, a burner block and a quench unit, and is described, for example, in Ullmanns Encyclopedia of Industrial Chemistry (5$^{th}$ Edition, Volume A1, pages 97-144) or US 005824834A.

According to Ullmanns Encyclopedia of Industrial Chemistry (Wiley-VCH Verlag, 2008, Acetylenes, pages 13-15), the industrial processes for preparing acetylene differ by the quench medium used, which may be water or oil.

The present invention relates to the process variant in which a quench oil is used as the quench medium for the rapid cooling of the cracking gas. The feedstocks are heated separately in preheaters. The feedstocks used are mixed in a mixing unit and supplied via a mixing diffuser to a burner and further to a combustion chamber. Downstream of the combustion chamber, nozzles are used to supply a quench oil to the cracking gas, which is cooled rapidly to about 200-250° C. The quench oil used is especially pyrolysis oil. This offers advantages in the recovery of heat from the cracking gas, which is utilized for raising steam.

With the suspension formed in the course of quenching, it is possible to discharge the soot obtained. Subsequently, the regenerated and cooled quench oil is sent back to the quench circuit.

The greatest advantage over the open water quench, however, is that the variant described enables a process closed with respect to the environment and hence avoids hydrocarbon emissions. The disadvantage of this variant is the tendency of the oils used to crack on contact with the cracking gas which is at up to 2000° C. As a result, the quench circuit must additionally be freed of these cracking products by costly and inconvenient cleaning and the oil which has thus been lost must be replaced.

In this process too, as a result of reaction, a relatively large wastewater stream is obtained, which is saturated with gases such as carbon monoxide, hydrogen, acetylene, higher acetylenes and BTX aromatics. The higher acetylenes are principally methyl-, vinyl- and diacetylene. The BTX aromatics are principally benzene, toluene, the xylene isomers, styrene and indene.

A wastewater with such contamination cannot be released into a water treatment plant without pretreatment since an explosive atmosphere can form as a result of outgassing, for example, in the sewer system too. Moreover, the dissolved hydrocarbons are a strain on the degradation rate even of an adapted water treatment plant.

It was therefore an object of the invention to provide a process for preparing acetylene and synthesis gas by partial oxidation of hydrocarbons, which ensures both a high yield of acetylene product of value and compliance with the applicable environmental protection regulations.

The object is achieved by a process for preparing acetylene and synthesis gas by partial oxidation of hydrocarbons with oxygen, in which a first input stream comprising one or more hydrocarbons and a second input stream comprising oxygen
are separately preheated,
mixed in a ratio of the mass flow rates of the second input stream to the first input stream corresponding to an oxygen ratio λ of less than or equal to 0.35, oxygen ratio λ being understood to mean the ratio of the amount of oxygen actually present in the second input stream to the stoichiometrically necessary amount of oxygen required for the complete combustion of the one or more hydrocarbons present in the first input stream,
supplied via a burner block to a combustion chamber in which the partial oxidation of the hydrocarbons takes place,
to obtain a cracking gas which is quenched to 200 to 250° C. downstream of the combustion chamber by injection of a quench oil, to obtain
a product gas stream $I_g$ which
is cooled with further quench oil in a burner column, by drawing off liquid from one or more suitable stages in the burner column, cooling it by indirect heat exchange with water to raise steam, and supplying it again to the burner column above the stage from which it was drawn off, to obtain
a product gas stream $II_g$ which has been cooled to 60° C. to 90° C. and which
is passed into a final cooler in which direct heat exchange with water gives a product gas stream $III_g$ cooled to 20° C. to 50° C., and a process water stream $I_{liq}$,
which comprises subjecting the discharged process water stream $I_{liq}$ to a cleaning operation by partial vaporization in a one-stage flash vessel, the process water stream $I_{liq}$ being vaporized in a proportion of 0.01% by weight to 10% by weight, based on the total weight thereof, to obtain a cleaned process water stream $II_{liq}$ which is disposed of in the wastewater.

BRIEF DESCRIPTION OF THE DRAWING

FIG. 1 schematically illustrates an embodiment of the invention.

It has been found that a partial vaporization of the combined process water streams in a one-stage flash vessel results in entrainment of the unwanted dissolved gases, especially polymerizable components, for example higher acetylenes, from the process water streams with the flash vapor into the gas phase, and these gases can be removed from the liquid phase to such an extent that it can be disposed of in the excess wastewater obtained.

The vapors of unwanted dissolved gases entrained with the flash vapor can subsequently, for example, after condensation of the water vapor, be incinerated or disposed of in the process in some other way.

It has been shown that, surprisingly, a one-stage flash for partial vaporization of the discharged process water stream in a proportion of 0.01 to 10% by weight, based on the total weight of the discharged process water stream, enables sufficient depletion of unwanted dissolved components, such that this process water can be disposed of safely and without any problems in the water treatment plant vie the sewer system.

According to the invention, the process for preparing acetylene and synthesis gas is conducted with an oxygen ratio λ of less than or equal to 0.35, the oxygen ratio λ being understood to mean the ratio of the amount of oxygen actually present in the second input stream to the stoichiometrically necessary amount of oxygen required for the complete combustion of the one or more hydrocarbons present in the first input stream.

In the case of operation with an oxygen ratio λ within the above range, a high yield of acetylene product of value is ensured.

The process is independent of the specific form of the reactor system comprising mixing unit, burner block and quench unit.

The reactor systems typically used are explained in detail hereinafter:

The starting materials, i.e. a gas stream comprising hydrocarbons, especially natural gas, and oxygen, are heated separately, typically up to 600° C. In a mixing unit, the reactants are mixed vigorously and, after flowing through a burner block, are reacted exothermically. The burner block typically consists of a multitude of parallel channels in which the flow rate of the ignitable oxygen/hydrocarbon mixture is higher than the flame speed, in order to prevent the flame from striking through into the mixing unit. The metallic burner block is cooled in order to withstand the thermal stresses. According to the residence time in the mixing unit, there is the risk of pre- and re-ignition due to the limited thermal stability of the mixtures. For this purpose, the term "ignition delay time" or "induction time" is used as the period of time within which an ignitable mixture does not undergo any significant intrinsic thermal change. The induction time depends on the nature of the hydrocarbons used, the mixing state, pressure and temperature. It determines the maximum residence time of the reactants in the mixing unit. Reactants such as hydrogen, liquefied gas or light gasoline, the use of which is particularly desirable due to yield and/or capacity increases in the synthesis process, feature comparatively high reactivity and hence a short induction time.

The acetylene burners being used on the current production scale are notable for the cylindrical geometry of the combustion chamber. The burner block has passage bores preferably in a hexagonal arrangement. In one embodiment, for example, 127 bores of internal diameter 27 mm are arranged hexagonally on a circular base cross section with a diameter of approx. 500 mm. In general, the channel diameters used are about 19 to 27 mm in diameter. The downstream combustion chamber in which the flame of the acetylene-forming partial oxidation reaction is stabilized is typically likewise of cylindrical cross section, is water-cooled and corresponds in terms of appearance to that of a short tube (for example of diameter 180 to 533 mm and length 380 to 450 mm). At the level of the burner block, what is called auxiliary oxygen is supplied to the combustion chamber both in the axial and in the radial direction. This ensures flame stabilization and hence a defined separation of the flame roots and hence of the commencement of reaction from the stopping of the reaction by the quench unit. The overall burner composed of burner block and combustion chamber is suspended from the top by means of a flange into a quench vessel of greater cross section. At the level of the exit plane from the combustion chamber, on the outer circumference thereof, are installed quench nozzles on one or more quench distributor rings, which atomize the quench medium with or without the aid of an atomization medium and inject it virtually at right angles to the main flow direction of the reaction gases leaving the combustion chamber. This direct quench has the task of cooling the reaction mixture extremely rapidly, such that further reactions, i.e. especially the degradation of acetylene formed, are frozen. The range and distribution of the quench jets is ideally such that a very homogeneous temperature distribution is achieved within a very short time.

The present industrial process forms, as well as acetylene, essentially hydrogen, carbon monoxide and soot. The soot particles formed in the flame front can adhere as seeds to the combustion chamber side walls, which then results, under suitable physicochemical conditions, in growth, deposition and caking of coke layers. These deposits are removed by mechanical cleaning periodically in the region of the combustion chamber walls by means of a poker unit.

The present invention makes use of the fact that, in the above process, a process water stream $I_{liq}$ is obtained at a temperature in the range between 60 and 96° C., preferably with a temperature in the range from approximately 70 to 80° C. The thermal energy present allows sufficient removal of unwanted dissolved gases by partial vaporization into vacuum.

The product gas stream $II_g$ is cooled especially to 70° C. to 80° C.

In the final cooler, direct heat exchange with water gives especially a product gas stream $III_g$ cooled to 30° C. to 40° C.

The partial vaporization is preferably effected by one-stage flashing into vacuum.

Further preferably, the partial vaporization by one-stage flashing is effected adiabatically.

In one process variant, the partial vaporization can advantageously be promoted by heat input.

Sufficient removal of the dissolved gases can also be achieved by means of a stripping column. For this purpose, the combined process water stream is introduced at the top of the column, and the stripping steam in countercurrent at the bottom of the stripping column. This process step too achieves sufficient depletion of the dissolved gases. The apparatus complexity and hence also the capital costs of the process step are much higher than in the case of the single, inventive flash. Moreover, the internals of the separation stages and distributors which are then necessary have much more of a tendency to be soiled by polymerizing components than the simple structure of a one-stage flash.

The flash vessel preferably has one stage and can be equipped with customary internals, such as structured packings or trays, and also with a demister to prevent droplet entrainment.

Also possible is a multistage flash or a heat input in the bottoms, as in a distillation column, rather than preheating of the feed.

Thus, this process constitutes a very inexpensive means of circulation water cleaning, or wastewater cleaning.

The vacuum can be generated in a manner known in the prior art, for example by means of a steam jet system or a water ring compressor. The offgas can then be treated further within the plant or else supplied to an offgas incineration.

The invention is illustrated in detail hereinafter by a drawing and a working example.

The sole FIGURE, FIG. 1 shows the schematic diagram of a preferred inventive plant.

The plant shown in FIG. 1 is supplied with a gas stream 1 comprising hydrocarbons and a gas stream 2 comprising oxygen, which are preheated separately by means of preheaters V1 and V2, supplied via a mixing unit and a burner block B to a combustion chamber F, to obtain a cracking gas which is quenched to 200-250° C. downstream of the combustion chamber F by injection of a quench oil to obtain a product gas stream $I_g$ which is cooled with further quench oil in a burner column BK, in two stages in the preferred embodiment shown in the FIGURE, raising steam through thermal integration, by indirect heat exchange with water. From the burner column BK, product gas stream $II_g$ cooled to 80° C. is drawn off overhead, and is supplied to a final cooler SK in which direct heat exchange with water gives a product gas stream $III_g$ cooled to 30° C., and a process water stream $I_{liq}$ for discharge, which is supplied to a one-stage flash vessel E, in which it is partially vaporized to obtain a cleaned process water stream $II_{liq}$ which is supplied to the water treatment plant. In order to prevent blockage of the quench nozzles, a comminution pump P for the soot suspended in the quench oil should be provided immediately below the burner column BK. For quench oil regeneration, a substream thereof is supplied to a stirred tank K which is heated to 500° C., and in which the volatile components vaporize and pure coke is drawn at the base thereof.

From the base of the final cooler SK, a liquid stream is drawn off and is separated in a decanter D into an oily fraction which comprises especially light aromatics (benzene/toluene/xylene) and is partly discharged, the rest being added again to the upper part of the burner column BK, and an aqueous fraction which is for the most part introduced as cooling medium at the top of the final cooler SK, and partly supplied as an excess process water stream $I_{liq}$ to the one-stage flash vessel E.

WORKING EXAMPLE

A process water stream $I_{liq}$ at 1.2 bar absolute and 57° C. is heated to 70° C. by addition of steam and then decompressed in one stage to 300 mbar absolute. This forms 0.62% flash steam based on the feed.

The following compositions and depletion rates are obtained:

|  | Wastewater before flash [ppm by wt.] | Wastewater after flash [ppm by wt.] | Depletion [%] |
| --- | --- | --- | --- |
| CO | 6.192 | 0.100 | 98.38% |
| Methane | 0.544 | 0.001 | 99.91% |
| Ethane | 0.000 | 0.000 | 100.00% |
| Ethylene | 0.117 | 0.000 | 99.71% |
| Acetylene | 9.190 | 0.232 | 97.47% |
| Propene | 0.006 | 0.000 | 99.75% |
| Propadiene | 0.015 | 0.000 | 99.75% |
| Propyne | 0.111 | 0.004 | 96.68% |
| Butenyne | 0.072 | 0.001 | 97.94% |
| Butadiyne | 0.453 | 0.047 | 89.70% |
| Benzene | 536.504 | 27.504 | 94.87% |
| Naphthalene | 0.001 | 0.000 | 94.87% |
| Indane | 28.239 | 3.246 | 88.50% |
| Indene | 104.010 | 13.342 | 87.17% |

Due to the high depletion of the combustible and toxic components, the wastewater stream after decompression can be released without risk into the sewer system to a water treatment plant.

The invention claimed is:

1. A process for preparing acetylene and synthesis gas by partial oxidation of hydrocarbons with oxygen, in which a first input stream (1) comprising one or more hydrocarbons and a second input stream (2) comprising oxygen are separately preheated;

mixing in a ratio of the mass flow rates, the second input stream (2) to the first input stream (1) corresponding to an oxygen ratio of less than or equal to 0.35, oxygen ratio being understood to mean the ratio of the amount of oxygen actually present in the second input stream (2) to the stoichiometrically necessary amount of oxygen required for the complete combustion of the one or more hydrocarbons present in the first input stream (1);

supplying the mixture via a burner block (B) to a combustion chamber (F) in which the partial oxidation of the hydrocarbons takes place, to obtain a cracking gas;

quenching the cracking gas to 200° C. to 250° C. downstream of the combustion chamber by injection of a quench oil, to obtain a product gas stream $I_g$;

cooling the product gas stream with further quench oil in a burner column (BK), by drawing off liquid from one or more suitable stages in the burner column (BK), cooling it by indirect heat exchange with water to raise steam, and supplying it again to the burner column (BK) above the stage from which it was drawn off to obtain a product gas stream $II_g$ which has been cooled to 60° C. to 90° C.;

passing the product gas stream $II_g$ into a final cooler (SK) in which direct heat exchange with water gives a product gas stream $III_g$ cooled to 20° C. to 50° C., and a process water stream $I_{liq}$; and subjecting the process water stream $I_{liq}$ to a cleaning operation by partial vaporization in a one-stage flash vessel, the process water stream $I_{liq}$ being vaporized in a proportion of 0.01% by weight to 10% by weight, based on the total weight thereof, to obtain a cleaned process water stream $II_{liq}$ which is disposed of in the wastewater.

2. The process according to claim 1, wherein the product gas stream $I_{liq}$ is cooled to 70° C. to 80° C.

3. The process according to claim 1, wherein direct heat exchange with water in the final cooler (SK) gives a product gas stream $III_g$ cooled to 30° C. to 40° C.

4. The process according to claim 1, wherein the process water stream $I_{liq}$ is evaporated in a proportion of 0.5% by weight to 2% by weight, based on the total weight thereof.

5. The process according to claim 1, wherein the partial vaporization is conducted by one-stage flashing into vacuum.

6. The process according to claim 5, wherein the partial vaporization by one-stage flashing is conducted adiabatically.

7. The process according to claim 1, wherein the partial vaporization is promoted by heat input.

8. The process according to claim 1, wherein the one-stage flash vessel (E) is equipped with structured packings, trays, or other internals.

9. The process according to claim 1, wherein the one-stage flash vessel (E) is equipped with a demister to prevent liquid droplet entrainment.

* * * * *